(12) United States Patent
Kamath (10) Patent No.: US 7,429,619 B2
(45) Date of Patent: Sep. 30, 2008

US007429619B2

(54) POLYACRYLIC FILM FORMING COMPOSITIONS

(75) Inventor: Satish Kamath, Hackettstown, NJ (US)

(73) Assignee: McNeil Consumer Healthcare, Fort Washington, PA (US)

( * ) Notice: Subject to any disclaimer, the term of this patent is extended or adjusted under 35 U.S.C. 154(b) by 494 days.

(21) Appl. No.: 10/211,139

(22) Filed: Aug. 2, 2002

(65) Prior Publication Data

US 2004/0022755 A1 Feb. 5, 2004

(51) Int. Cl.
*A61K 47/00* (2006.01)

(52) U.S. Cl. .................. 514/772.1; 514/772; 514/772.2; 514/772.6; 424/400

(58) Field of Classification Search .................. None
See application file for complete search history.

(56) References Cited

U.S. PATENT DOCUMENTS

| | | | |
|---|---|---|---|
| 1,787,777 A | 1/1931 | Colton | |
| 3,185,626 A | 5/1965 | Baker | |
| 3,751,277 A | 8/1973 | Small et al. | |
| 3,802,896 A * | 4/1974 | Westall et al. | 523/100 |
| 4,001,211 A | 1/1977 | Sarkar | |
| 4,267,164 A | 5/1981 | Yeh et al. | |
| 4,313,765 A | 2/1982 | Baird et al. | |
| 4,543,370 A | 9/1985 | Porter et al. | |
| 4,572,833 A | 2/1986 | Pedersen et al. | |
| 4,576,646 A | 3/1986 | Branco et al. | |
| 4,601,894 A | 7/1986 | Hanna et al. | |
| 4,643,894 A | 2/1987 | Porter et al. | |
| 4,652,313 A | 3/1987 | Den Boer et al. | |
| 4,661,162 A | 4/1987 | Kurihara et al. | |
| 4,683,256 A | 7/1987 | Porter et al. | |
| 4,690,822 A * | 9/1987 | Uemura et al. | 424/455 |
| 4,695,467 A | 9/1987 | Uemura et al. | |
| 4,695,591 A | 9/1987 | Hanna et al. | |
| 4,725,441 A | 2/1988 | Porter et al. | |
| 4,775,536 A | 10/1988 | Patell | |
| 4,802,924 A | 2/1989 | Woznicki et al. | |
| 4,816,259 A | 3/1989 | Matthews et al. | |
| 4,820,524 A | 4/1989 | Berta | |
| 4,828,841 A | 5/1989 | Porter et al. | |
| 4,853,230 A | 8/1989 | Lovgren et al. | |
| 4,853,249 A | 8/1989 | Takashima et al. | |
| 4,880,636 A | 11/1989 | Franz | |
| 4,886,669 A | 12/1989 | Ventouras | |
| 4,892,742 A | 1/1990 | Shah | |
| 4,897,270 A | 1/1990 | Deutsch et al. | |
| 4,913,893 A * | 4/1990 | Varco et al. | 424/47 |
| 4,917,885 A | 4/1990 | Chiba et al. | |
| 4,948,622 A | 8/1990 | Kokubo et al. | |
| 4,965,089 A | 10/1990 | Sauter et al. | |
| 4,981,698 A | 1/1991 | Cherukuri et al. | |
| 4,999,189 A | 3/1991 | Kogan et al. | |
| 5,009,897 A | 4/1991 | Brinker et al. | |
| 5,023,108 A | 6/1991 | Bagaria et al. | |
| 5,026,560 A | 6/1991 | Makino et al. | |
| 5,059,416 A | 10/1991 | Cherukuri et al. | |
| 5,064,650 A | 11/1991 | Lew | |
| 5,077,053 A | 12/1991 | Kuncewitch et al. | |
| 5,082,669 A | 1/1992 | Shirai et al. | |
| 5,098,715 A | 3/1992 | McCabe et al. | |
| 5,146,730 A | 9/1992 | Sadek et al. | |
| 5,164,195 A | 11/1992 | Lew | |
| 5,186,930 A | 2/1993 | Kogan et al. | |
| 5,198,227 A | 3/1993 | Batista et al. | |
| 5,209,933 A | 5/1993 | MacFarlane et al. | |
| 5,213,738 A | 5/1993 | Hampton et al. | |
| 5,228,909 A | 7/1993 | Burdick et al. | |
| 5,228,916 A | 7/1993 | Berta | |
| 5,248,516 A | 9/1993 | Wheatley et al. | |
| 5,252,339 A | 10/1993 | Cristofori et al. | |
| 5,286,502 A | 2/1994 | Meyers | |
| 5,296,233 A | 3/1994 | Batista et al. | |
| 5,382,435 A | 1/1995 | Geary et al. | |
| 5,393,333 A | 2/1995 | Trouve | |
| 5,409,711 A | 4/1995 | Mapelli et al. | |
| 5,411,746 A | 5/1995 | Signorino et al. | |
| 5,415,871 A | 5/1995 | Pankhania et al. | |
| 5,422,121 A | 6/1995 | Lehmann et al. | |
| 5,425,950 A | 6/1995 | Danidiker et al. | |
| 5,433,960 A | 7/1995 | Meyers | |
| 5,436,026 A | 7/1995 | Berta | |
| 5,445,829 A | 8/1995 | Paradissis et al. | |
| 5,447,726 A | 9/1995 | Nomura | |
| 5,459,983 A | 10/1995 | Sadek et al. | |
| 5,464,633 A | 11/1995 | Conte et al. | |

(Continued)

FOREIGN PATENT DOCUMENTS

EP        0056825  B1     8/1982

(Continued)

OTHER PUBLICATIONS

Remington: "The Science & Practice of Pharmacy", pp. 208-209 (2000).

(Continued)

*Primary Examiner*—Michael G. Hartley
*Assistant Examiner*—Eric E. Silverman (57) ABSTRACT

Water soluble, gelatin-free dip coatings for substrates comprising an acrylic film former; a paraben plasticizer; and a secondary plasticizer such as polyvinylpyrrolidone, polyethylene glycol 300, polyethylene glycol 400 or mixtures thereof.

25 Claims, 1 Drawing Sheet

U.S. PATENT DOCUMENTS

| | | | |
|---|---|---|---|
| 5,470,581 A | 11/1995 | Grillo et al. |
| 5,474,786 A | 12/1995 | Kotwal et al. |
| 5,480,479 A | 1/1996 | Signorino |
| 5,482,718 A | 1/1996 | Shah et al. |
| 5,496,561 A | 3/1996 | Okada et al. |
| 5,506,248 A | 4/1996 | Nikfar et al. |
| 5,512,314 A | 4/1996 | Signorino et al. |
| 5,514,384 A | 5/1996 | Signorino |
| 5,525,354 A | 6/1996 | Posti et al. |
| 5,534,263 A | 7/1996 | Wong et al. |
| 5,538,125 A | 7/1996 | Berta |
| 5,560,926 A | 10/1996 | Franz et al. |
| 5,571,533 A | 11/1996 | Santus et al. |
| 5,591,455 A | 1/1997 | Signorino |
| 5,593,694 A | 1/1997 | Hayashida et al. |
| 5,595,592 A | 1/1997 | Signorino et al. |
| 5,614,218 A | 3/1997 | Olsson et al. |
| 5,622,721 A | 4/1997 | Dansereau et al. |
| 5,630,871 A | 5/1997 | Jordan |
| 5,633,015 A | 5/1997 | Gilis et al. |
| 5,635,208 A | 6/1997 | Parekh et al. |
| 5,641,513 A | 6/1997 | Lech et al. |
| 5,641,536 A | 6/1997 | Lech et al. |
| 5,650,169 A | 7/1997 | Conte et al. |
| 5,658,589 A | 8/1997 | Parekh et al. |
| 5,667,573 A | 9/1997 | Kondou |
| 5,667,802 A | 9/1997 | Grimberg |
| 5,679,406 A | 10/1997 | Berta |
| 5,681,585 A | 10/1997 | Oshlack et al. |
| 5,681,684 A | 10/1997 | Kinashi et al. |
| 5,685,589 A | 11/1997 | Kikuchi et al. |
| 5,690,960 A | 11/1997 | Bengtsson et al. |
| 5,698,220 A | 12/1997 | Cardinal et al. |
| 5,707,648 A | 1/1998 | Yiv |
| 5,712,310 A | 1/1998 | Koch |
| 5,725,880 A | 3/1998 | Hirakawa et al. |
| 5,733,575 A | 3/1998 | Mehra et al. |
| 5,738,874 A | 4/1998 | Conte et al. |
| 5,750,148 A | 5/1998 | Maruyama et al. |
| 5,756,123 A | 5/1998 | Yamamoto et al. |
| 5,770,225 A | 6/1998 | Parekh et al. |
| 5,776,479 A | 7/1998 | Pallos et al. |
| 5,792,473 A | 8/1998 | Gergely et al. |
| 5,800,836 A | 9/1998 | Morella et al. |
| 5,807,580 A | 9/1998 | Luber |
| 5,814,336 A | 9/1998 | Kelm et al. |
| 5,814,339 A | 9/1998 | Prudhoc |
| 5,830,503 A | 11/1998 | Chen |
| 5,843,479 A | 12/1998 | Kelm et al. |
| 5,863,559 A | 1/1999 | Phillips et al. |
| 5,885,617 A | 3/1999 | Jordan |
| 5,891,474 A | 4/1999 | Busetti et al. |
| 5,908,638 A | 6/1999 | Huber et al. |
| 5,914,132 A | 6/1999 | Kelm et al. |
| 5,919,485 A | 7/1999 | Cochran et al. |
| 5,922,352 A | 7/1999 | Chen et al. |
| 5,935,602 A | 8/1999 | Dansereau et al. |
| 5,945,124 A | 8/1999 | Sachs et al. |
| 5,968,551 A | 10/1999 | Oshlack et al. |
| 6,022,564 A * | 2/2000 | Takechi et al. ............... 424/489 |
| 6,039,976 A | 3/2000 | Mehra et al. |
| 6,051,255 A | 4/2000 | Conley et al. |
| 6,066,336 A | 5/2000 | Ullah et al. |
| 6,068,856 A | 5/2000 | Sachs et al. |
| 6,077,533 A | 6/2000 | Oshlack et al. |
| 6,077,541 A | 6/2000 | Chen et al. |
| 6,080,426 A | 6/2000 | Amey et al. |
| 6,083,430 A * | 7/2000 | Fuisz et al. .................... 264/5 |
| 6,096,340 A | 8/2000 | Chen et al. |
| 6,113,945 A | 9/2000 | Jacobs et al. |
| 6,120,801 A | 9/2000 | Parekh et al. |
| 6,120,802 A | 9/2000 | Breitenbach et al. |
| 6,123,964 A | 9/2000 | Asghamejad et al. |
| 6,129,933 A | 10/2000 | Oshlack et al. |
| 6,156,343 A | 12/2000 | Morita et al. |
| 6,165,513 A | 12/2000 | Dansereau et al. |
| 6,183,808 B1 | 2/2001 | Grillo et al. |
| 6,190,692 B1 | 2/2001 | Busetti et al. |
| 6,210,714 B1 | 4/2001 | Oshlack et al. |
| 6,214,376 B1 | 4/2001 | Gennadios |
| 6,214,380 B1 | 4/2001 | Parekh et al. |
| 6,228,400 B1 | 5/2001 | Lee et al. |
| 6,238,704 B1 | 5/2001 | Suzuki et al. |
| 6,245,350 B1 | 6/2001 | Amey et al. |
| 6,245,356 B1 | 6/2001 | Baichwal |
| 6,248,363 B1 | 6/2001 | Patel et al. |
| 6,270,804 B1 | 8/2001 | Getz et al. |
| 6,274,162 B1 | 8/2001 | Steffenino et al. |
| 6,274,173 B1 | 8/2001 | Sachs et al. |
| 6,294,200 B1 | 9/2001 | Conte et al. |
| 6,309,666 B1 | 10/2001 | Hatano et al. |
| 6,309,668 B1 | 10/2001 | Bastin et al. |
| 6,340,473 B1 * | 1/2002 | Tanner et al. ............... 424/451 |
| 6,348,090 B1 | 2/2002 | Grillo et al. |
| 6,420,473 B1 | 7/2002 | Chittamuru et al. |
| 6,521,257 B1 | 2/2003 | Taniguchi et al. |
| 6,579,545 B2 | 6/2003 | Zyck et al. |
| 6,635,282 B1 | 10/2003 | Flanagan et al. |
| 2001/0000471 A1 | 4/2001 | Shen et al. |
| 2001/0036476 A1 | 11/2001 | Oshlack et al. |
| 2001/0046511 A1 | 11/2001 | Zerbe et al. |

FOREIGN PATENT DOCUMENTS

| | | |
|---|---|---|
| EP | 246693 B1 | 11/1987 |
| EP | 0470872 B1 | 2/1992 |
| EP | 0575179 A | 12/1993 |
| EP | 0638310 | 2/1995 |
| EP | 0 684 301 A2 | 11/1995 |
| EP | 0 717 992 A2 | 6/1996 |
| EP | 714656 A | 6/1996 |
| EP | 0714656 A | 6/1996 |
| EP | 0 733 367 A | 9/1996 |
| EP | 974344 A2 | 1/2000 |
| EP | 0 934 734 B1 | 10/2002 |
| FR | 2 783 832 A | 3/2000 |
| GB | 1543167 | 3/1979 |
| JP | 63062535 A | 3/1988 |
| JP | 10066556 A | 3/1998 |
| WO | WO 9007859 A | 7/1990 |
| WO | WO 9115548 A | 10/1991 |
| WO | WO 93/09785 A | 5/1993 |
| WO | WO 95/03063 A | 2/1995 |
| WO | WO 95/23594 A1 | 9/1995 |
| WO | 0839527 A | 5/1998 |
| WO | WO 98/30341 A | 7/1998 |
| WO | WO 99/03449 A | 1/1999 |
| WO | WO 99/46329 A1 | 9/1999 |
| WO | WO 00/18835 A | 4/2000 |
| WO | WO 00/18835 A1 | 4/2000 |
| WO | WO 00/32174 A2 | 6/2000 |
| WO | WO 00/42998 A1 | 7/2000 |
| WO | WO 00/45794 A1 | 8/2000 |
| WO | WO 00/48574 A1 | 8/2000 |
| WO | WO 01/03677 A | 1/2001 |
| WO | WO 0103677 A | 1/2001 |
| WO | WO 01/07507 A1 | 2/2001 |
| WO | WO 01/26633 A1 | 4/2001 |
| WO | WO 01/26634 A | 4/2001 |
| WO | WO 01/37816 A | 5/2001 |

WO    WO 01/91721 A2    12/2001

OTHER PUBLICATIONS

Remington: "The Science & Practice of Pharmacy", pp. 1625-1630 (17th Ed.) (1985).
Fegely, K., "The Effect of Tablet Shape on the Perception of High Gloss Film Coating Systems", www.colorcon.com (2002).
Tricor Systems WGloss 3.4 Model 805A/806H Surface Analysis System Reference Manual (1996).
"Purity® Gum 59" Technical Services Bulletin, 1993.
Zallie, "The Role and Function of Specialty Starches in the Confection Industry" Brochure, pp. 1-16 (1997).
Zallie, "New Starches for Gelling and Non-gelling Applications" reprinted from Manufacturing Confectioner (Nov. 1988).
FMC Biopolymer Brochure, "Carragenan", available at www.fmcbiopolymer.com on Apr. 3, 2001.
Polyvinytpyrrolidone for the Pharmaceutical Industry, Brochure by BASF, pp. 15 and 107-108 (Aug. 1993).
Specifications and Test Methods for EUDRAGIT®, pp. 1-3 (1996).
Applicability of the Monograh . . . EUDRAGIT® S30D, pp. 1 (1994).
Gulian, Frank et al., "Color and Gloss Uniformity of Tablets Coated in a Side-Vented Pan Using Opaglos® 2"; Poster Reprint, American Association of Pharmaceutical Scientists, pp. 1-5, Oct. 2001.
Light, "Modified Food Starches: Why, What, Where and How", (adapted from Modified Food Starch's Symposium at AACCs 74th Annual Meeting Oct. 29-Nov. 2, 1989).
Pharmacia Remington, Preformulacion, pp. 2241-2242.
European Search Report dated Dec. 3, 2003 for EP 03254789.

* cited by examiner

POLYACRYLIC FILM FORMING COMPOSITIONS

FIELD OF THE INVENTION

This invention relates to novel, water soluble, gelatin-free compositions for coating substrates, such as tablets and capsules, and methods for producing such dosage forms. This invention further relates to a method for increasing the weight gain of a water soluble, gelatin-free, film forming coating on a dip-coated tablet or caplet.

BACKGROUND OF THE INVENTION

During most of this century, hard gelatin capsules were a popular dosage form for prescription and over-the-counter (OTC) drugs. The ability to combine capsule halves having different colors provided manufacturers with a unique means of distinguishing various pharmaceutical products. Many patients preferred capsules over tablets, perceiving them as being easier to swallow. This consumer preference prompted pharmaceutical manufacturers to market certain products in capsule form even when they were also available in tablet form.

Generally, empty hard gelatin capsules are manufactured using automated equipment. This equipment employs rows of stainless steel pins, mounted on bars or plates, which are dipped into a gelatin solution maintained at a uniform temperature and fluidity. The pins are then withdrawn from the gelatin solution, rotated, and then inserted into drying kilns through which a strong blast of filtered air with controlled humidity is forced. A crude capsule half is thus formed over each pin during drying. Each capsule half is then stripped, trimmed to uniform length, filled and joined to an appropriate mating half.

An alternative to capsule products are caplets, which are solid, oblong tablets that may be coated with various polymers such as cellulose ethers to improve their aesthetics, stability, and swallowability. Typically, such polymers are applied to the tablets either from solution in organic solvents, or from aqueous dispersion via spraying. However, such spray-coated tablets lack the shiny surface and elegance of the hard gelatin capsules. Additionally, it is not commercially feasible to spray-coat a tablet with a differant color coating on each end.

Another alternative to capsule products are "gelcaps," which are elegant, shiny, consumer-preferred dosage forms that are prepared by dipping each half of an elongated tablet in two different colors of gelatin solution. See U.S. Pat. Nos.: 4,820,524; 5,538,125; 5,685,589; 5,770,225; 5,198,227; and 5,296,233, which are all incorporated by reference herein. A similar dosage form, commercially available as a "geltab," is prepared by dipping each half of a round, convex tablet into different colors of gelatin solution, as described in U.S. Pat. No. 5,228,916, U.S. Pat. No. 5,436,026 and U.S. Pat. No. 5,679,406, which are all incorporated by reference herein. As used herein, such "gelcaps" and "geltabs" shall be included within the broader term, "tablets."

However, the use of gelatin as a pharmaceutical coating material presents certain disadvantages and limitations, including the potential for decreased dissolution rate after extended storage due to cross-linking of the gelatin, potential for microbial contamination of the gelatin solution during processing, and long processing times due to extensive drying requirements. Further, the energy-related costs associated with gelatin coatings tend to be high since the gelatin material is typically applied to the substrates at an elevated temperature of at least about 40° C. in order to maintain fluidity of the gelatin, while the substrates are maintained at about 50° C. in order to minimize microbial growth.

Various attempts have been made to produce gelatin-free hard shell capsules. For example, WO 00/18835 discloses the combination of starch ethers or oxidized starch and hydrocolloids for use in preparing hard capsule shells via conventional dip molding processing. See also U.S. Pat. No. 4,001,211 (capsules prepared via pin dip coating with thermogelled methylcellulose ether compositions). However, due to potential tampering concerns, hard gelatin capsules are no longer a preferred delivery system for consumer (over-the-counter) pharmaceuticals, dietary supplements, or other such products. Additionally, the properties of an ideal composition into which steel pins are to be dipped then dried to form hard capsule shells thereon are not necessarily the same as those for dipping tablets to form a coating thereon. For example, relevant physical properties such as viscosity, weight-gain, film thickness, tensile strength, elasticity, and moisture content will differ between compositions for hard capsule formation and for coating tablets. See e.g., U.S. Pat. No. 1,787,777 (Optimal temperatures of the substrate and coating solution, residence times in the solution, and drying conditions differ.)

One disadvantage associated with dipping tablets or capsules into a non-gelatin coating system is that the resulting coatings often lack adequate tensile strength, plasticity, hardness, and thickness. Moreover, the inclusion of plasticizers into such non-gelatin coating systems often results in tablets having soft, tacky coatings without a hardness sufficient to maintain their shape or smoothness during handling. In addition, many non-gelatin compositions do not adhere to the tablet substrate in an amount sufficient to uniformly cover the tablet after a single dipping. Further, many non-gelatin compositions lack the sufficient rheological properties necessary to maintain uniform color dispersion throughout the dipping and drying process. Although attempts have been made to improve the rheological properties of these compositions by, for example, increasing their solids content in order to increase viscosity. However, such compositions often disadvantageously resulted in undesirable coating aesthetics such as surface roughness, decreased gloss, and non-uniform coating thickness.

It is desirable to find a coating material, and in particular a dip coating material, which not only produces a similar elegant, shiny, high gloss, consumer-preferred dosage form similar to that of gelatin-coated forms, but which is absent the limitations of gelatin, particularly those noted above.

SUMMARY OF THE INVENTION

This invention relates to a film forming composition comprised of, consisting of, and/or consisting essentially of a film forming composition comprised of, consisting of, and/or consisting essentially of, based upon the total dry solids weight of the composition:

a) from about 10 percent to about 70 percent of a film former comprised of a polymer or copolymer of acrylic acid or a derivative thereof, or a mixture of the polymer or copolymer of acrylic acid or a derivative thereof;

b) from about 2 percent to about 20 percent of a primary plasticizer comprised of a paraben; and c) from about 1 percent to about 50 percent of a secondary plasticizer selected from the group consisting of polyvinylpyrrolidone, polyethylene glycol 300, polyethylene glycol 400, pharmaceutically acceptable salts thereof, and mixtures thereof;

wherein the composition possesses a surface gloss of at least 150 gloss units when applied via dip coating to a substrate.

Another embodiment of the present invention is directed to a film forming composition comprised of, consisting of, and/or consisting essentially of, based upon the total dry solids weight of the composition:

a) from about 10 percent to about 70 percent of a film former comprised of a polymer or copolymer of acrylic acid or a derivative thereof, or a mixture of the polymer or copolymer of acrylic acid or a derivative thereof; and b) from about 3 percent to about 70 percent of a plasticizer selected from the group consisting of triacetin, acetylated monoglyceride, rape oil, olive oil, sesame oil, acetyltributyl citrate, glycerin sorbitol, diethyloxalate, diethylmalate, diethyl fumarate, dibutyl succinate, diethylmalonate, dioctylphthalate, dibutylsuccinate, triethylcitrate, tributylcitrate, glyceroltributyrate, propylene glycol, polyethylene glycols, hydrogenated castor oil, fatty acids, substituted triglycerides and glycerides, methyl paraben, ethyl paraben, propyl paraben, butyl paraben, polyvinylpyrrolidone, polyethylene glycol 300, polyethylene glycol 400, and pharmaceutically acceptable salts thereof and mixtures thereof, wherein the composition possesses a surface gloss of at least 150 when applied via dip coating to a substrate.

Yet another embodiment of the present invention is directed to a pharmaceutical dosage form comprising, consisting of, and/or consisting essentially of a core and a coating, said coating covering at least a portion of said core and having a surface gloss of at least 150 gloss units, wherein the coating comprises, consists of, and/or consists essentially of a) from about 10 percent to about 70 percent of a film former comprised of a polymer or copolymer of acrylic acid or a derivative thereof, or a mixture of the polymer or copolymer of acrylic acid or a derivative thereof;

b) from about 2 percent to about 20 percent of a primary plasticizer comprised of a paraben; and c) from about 1 percent to about 50 percent of a secondary plasticizer selected from the group consisting of polyvinylpyrrolidone, polyethylene glycol 300, polyethylene glycol 400, pharmaceutically acceptable salts thereof, and mixtures thereof.

We have found that when a dosage form is coated with the composition of the present invention, the result is an elegant, shiny, high gloss, consumer-preferred dosage form similar to that of a gelatin-coated form, but which lacks the limitations associated with gelatin, particularly those noted above. We have also found that when such a composition is used in dip coating and operations, it does not inhibit the dissolution of the active coated therewith. Further, we have found that the color uniformity of dosage forms coated with such compositions is improved upon the addition of a weight gain enhancer thereto.

DETAILED DESCRIPTION OF THE INVENTION

As used herein, the term "dosage form" applies to any solid, semi-solid, or liquid composition designed to contain a specific pre-determined amount (dose) of a certain ingredient, such as, for example, an active ingredient as defined below. Suitable dosage forms may be in the form of pharmaceutical drug delivery systems, including those for oral administration, buccal administration, rectal administration, topical, transdermal, or mucosal delivery, or subcutaneous implants, or other implanted drug delivery systems; or compositions for delivering minerals, vitamins and other nutraceuticals, oral care agents, flavorants, and the like.

In one embodiment, the dosage form of the present invention may be in a solid form, yet may also contain liquid or semi-solid components therein.

In one embodiment, the dosage form may be an orally administered system for delivering a pharmaceutical active ingredient to the gastrointestinal tract of a human. In another embodiment, the dosage form may be an orally administered "placebo" system consisting essentially of pharmaceutically inactive ingredients, which is designed to have the same visual appearance as a particular pharmaceutically active dosage form. Such "placebo" system dosage forms are suitable for use as as control dosage forms in clinical studies, and in particular, those studies designed for testing the safety and efficacy of a particular pharmaceutically active ingredient.

As used herein, "substrate" refers to a surface, layer or underlying base or support upon which another substance resides or acts, and "core" refers to a substrate that is at least partially enveloped or surrounded by another material. As used herein, "capsules" refer to hard shell compartments that enclose a dosable ingredient. "Tablets," as used herein, refer to compressed or molded solid dosage forms of any shape or size. "Caplets," as used herein, refer to solid, oblong-shaped tablets. "Gelcaps" refer to solid caplets having a glossy gelatinous coating, and "geltabs" refer to solid tablets having flat sides, convex opposing faces, and a glossy gelatinous coating. "Hardness" as used herein in connection with films or coatings indicates the resistance of the film/coating to deformation upon impact. "Water soluble" or "water solubilize," as used herein in connection with non-polymeric materials, shall mean from sparingly soluble to very soluble, i.e., not more than 100 parts water required to dissolve 1 part of the non-polymeric, water soluble solute. See Remington, "The Science and Practice of Pharmacy," pages 208-209 (2000). "Water soluble" or "water solubilize," as used herein in connection with polymeric materials, shall mean that the polymer swells in water and can be dispersed at the molecular level to form a homogeneous dispersion or colloidal solution. "Surface gloss" as used herein, shall refer to amount of light reflectance as measured at a 60 degree incident angle using the method set forth in Example 4 herein.

Dimethicone is a well known pharmaceutical material consisting of linear siloxane polymers containing repeating units of the formula $\{-(CH_2)_2SiO\}_n$ stabilized with trimethylsiloxy end blocking units of the formula $[(CH_3)_3SiO-]$. Simethicone is the mixture of dimethicone and silicon dioxide. For the purposes of this invention, the two materials may be used interchangably.

The first embodiment of this invention is directed to water soluble, substantially gelatin-free, film forming compositions for coating tablets or other substrates. One composition comprises, consists of, and/or consists essentially of: a) a film former such as a polymer or copolymer of acrylic acid or derivative thereof such as methacrylic acid; b) a primary plasticizer such as a paraben; c) a secondary plasticizer such as polyvinylpyrrolidone, polyethylene glycol; and d) a solvent such as water. As used herein, "substantially gelatin-free" shall mean less than about 1 percent, e.g. less than about 0.5 percent, of gelatin in the composition.

The first component of the composition of the present invention is a film former, which may be comprised of acrylic-based polymers and copolymers, derivatives thereof, or mixtures thereof. "Copolymers," as used herein, shall mean a chemical compound or mixture thereof formed by polymerization and containing two or more repeating units. Examples of such film formers include those commercially available from Rohm Pharma GmbH, such as poly(ethyl acrylate, methyl methacrylate, trimethylammonioethyl methacrylate chloride) in a 1:2:0.1 weight ratio available under the tradename, "Eudragit RS;" poly(methacrylic acid, methyl methacrylate) in a 1:2 weight ratio available under the tradename, "Eudragit S;" and poly(methacrylic acid, methyl methacrylate) in a 1:1 weight ratio available under the tradename, "Eudragit L." More specific examples of film formers that are commercially available from Rohm Pharma GmbH include, but are not limited to, poly(ethyl acrylate, methyl methacrylate, trimethylammonioethyl methacrylate chloride), which is available under the tradename, "Eudragit RS30D;" poly(methacrylic acid, ethyl acrylate), which is available under the tradename, "Eudragit L30D;" poly(ethyl acrylate, methyl methacrylate), which is available under the tradename "Eudragit NE30D;" poly(ethyl acrylate, methyl methacrylate, trimethylammonioethyl methacrylate chloride, which is available under the tradename, "Eudragit RL;" and copolymers and mixtures thereof. Other film formers include, but are not limited to, polymers and copolymers of methacrylic acid, derivatives of polymers and copolymers of methacrylic acid such as ammoniomethacrylate copolymers, as well as copolymers thereof, derivatives thereof, and mixtures thereof.

In one embodiment, the composition includes a film former selected from the Eudragit RS30D polymer, the Eudragit RL30D polymer, copolymers thereof, and mixtures thereof. One suitable mixture may comprise Eudragit RS30D: Eudragit RL30D in about a 25:75 to about a 75:25 weight ratio.

The second component of the composition of the present invention is a plasticizer. Examples of suitable plasticizers include, but are not limited to triacetin, acetylated monoglyceride, rape oil, olive oil, sesame oil, acetyltributyl citrate, glycerin sorbitol, diethyloxalate, diethylmalate, diethyl fumarate, dibutyl succinate, diethylmalonate, dioctylphthalate, dibutylsuccinate, triethylcitrate, tributylcitrate, glyceroltributyrate, propylene glycol, polyethylene glycols such as polyethylene glycol 300 and polyethylene glycol 400, hydrogenated castor oil, fatty acids, substituted triglycerides and glycerides, methyl paraben, ethyl paraben, propyl paraben, butyl paraben, polyvinylpyrrolidone, and pharmaceutically acceptable salts thereof and mixtures thereof.

In one embodiment the plasticizer includes a primary plasticizer, which may be selected from methyl paraben, ethyl paraben, propyl paraben, butyl paraben, and pharmaceutically acceptable salts thereof or mixtures thereof, and a secondary plasticizer, which may be selected from polyvinylpyrrolidone, polyethylene glycol 300, polyethylene glycol 400, and pharmaceutically acceptable salts thereof, or mixtures thereof. Examples of suitable polyvinylpyrrolidones include but are not limited to that available from BASF Akteingesellschaft under the tradenames, "PVP K30" or "PVP K90". The "K value" for the polyvinylpyrrolidone refers to the average molecular weight of the compound as discussed on page 15 of the "Polyvinylpyrrolidone for the Pharmaceutical Industry" brochure by BASF (August 1993), which is incorporated by referenced herein.

In one embodiment, the film forming composition for coating substrates may be substantially free of gelatin, i.e., e.g. contains less than about 1%, or less than about 0.01% of gelatin.

In another embodiment, the film forming composition for coating substrates may be substantially free of bovine derived materials, i.e., e.g. contains less than about 1%, or less than about 0.01% of bovine derived materials.

In one embodiment, the film forming composition for coating substrates contains, based upon the total dry solids weight of the composition, from about 10 percent to about 70 percent, e.g. from about 40 percent to about 65 percent, of a film former; and from about 3 percent to about 70 percent, e.g. from about 20 percent to about 50 percent, of a plasticizer.

In another embodiment, the film forming composition for coating substrates contains, based upon the total dry solids weight of the composition, from about 10 percent to about 70 percent, e.g. from about 40 percent to about 65 percent, of a film former; from about 2 percent to about 20 percent, e.g. from about 5 percent to about 15 percent, of a primary plasticizer; and from about 1 percent to about 50 percent, e.g. from about 15 percent to about 35 percent, of a secondary plasticizer.

These film forming compositions are typically in the form of a dispersion for ease of dip coating substrates therein. Such dispersions contain a solvent in an amount, based upon the total weight of the dispersion, from about 65 percent to about 95 percent, for example, from about 75 percent to about 85 percent. Examples of suitable solvents include, but are not limited to water; alcohols such as methanol, ethanol, and isopropanol; organic solvents such as methylene chloride, acetone, and the like; and mixtures thereof. In one embodiment, the solvent is water. The resulting film forming dispersion typically possesses a solids level of, based upon the total weight of the film forming dispersion, from about 5 percent to about 35 percent, for example, from about 20 percent to about 30 percent.

In one embodiment, the film forming composition for coating substrates contains, based upon the total wet weight of the dipping dispersion composition, from about 2 percent to about 20 percent, e.g. from about 7 percent to about 15 percent, of a film former; from about 0.4 percent to about 5 percent, e.g. from about 1 percent to about 4 percent, of a primary plasticizer; from about 0.2 percent to about 12 percent, e.g. from about 2 percent to about 10 percent, of a secondary plasticizer; and from about 65 percent to about 95 percent, e.g. from about 70 percent to about 85 percent of water.

Optionally, the composition for coating substrates may further comprise other ingredients such as adjuvants and excipients, including opacifying agents, coloring agents, stabilizers, preservatives, flavorants, sweeteners and the like as known in the art. In one embodiment, the composition for coating substrates may further comprise, based upon the total weight of the dipping solution, from about 0 percent to about 14 percent opacifying agents such as titanium dioxide and/or colorants. See *Remington's Practice of Pharmacy*, Martin & Cook, $17^{th}$ ed., pp. 1625-30, which is herein incorporated by reference.

Any coloring agent suitable for use in pharmaceutical applications may be used in the present invention and may include, but not be limited to azo dyes, quinopthalone dyes, triphenylmethane dyes, xanthene dyes, indigoid dyes, iron oxides, iron hydroxides, titanium dioxide, natural dyes, and mixtures thereof. More specifically, suitable colorants include, but are not limited to patent blue V, acid brilliant green BS, red 2G, azorubine, ponceau 4R, amaranth, D&C red 33, D+C red 22, D+C red 26, D+C red 28, D+C yellow 10, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, antyhocyanines, turmeric, cochineal extract, clorophyllin, canthaxanthin, caramel, betanin, and mixtures thereof.

In one embodiment, the final product is a pharmaceutical dosage form comprised of a) a core; b) an optional subcoating layer that substantially covers the core; and c) an exterior coating layer that substantially covers the surface of the subcoating layer, the exterior coating layer comprised of the coating composition of the present invention. As used herein, "substantially covers" shall mean at least about 95 percent of the underlying surface area of the substrate or core is covered by the coating. In such embodiments the dosage form typically comprises at least one active ingredient. One or more active ingredients may be contained in the core, the subcoating layer, the exterior coating layer, or any combination thereof. In one embodiment, at least one active ingredient is contained in the core.

In another embodiment, a first active ingredient may be contained in the subcoating layer, and the core may contain a second active ingredient and/or an additional amount of the first active ingredient. In yet another embodiment, the active ingredient may be contained in the subcoating layer, and the core may be substantially free, i.e., contain less than about 1 percent, e.g. less than about 0.1 percent, of active ingredient.

In another embodiment, the pharmaceutical dosage form is comprised of: a) a core; b) an optional subcoating layer on the surface of the core that covers a portion of the core; and c) an exterior coating layer that covers a portion of the surface of the subcoating layer, with the exterior coating layer comprised of the film forming composition of the present invention. The exterior coating layer may or may not be visually similar to the subcoating layer. As used herein, "portion" shall mean a part of the dosage form having a surface area that is equal to or less than about 95 percent of the surface area of the underlying substrate.

Figure 2:
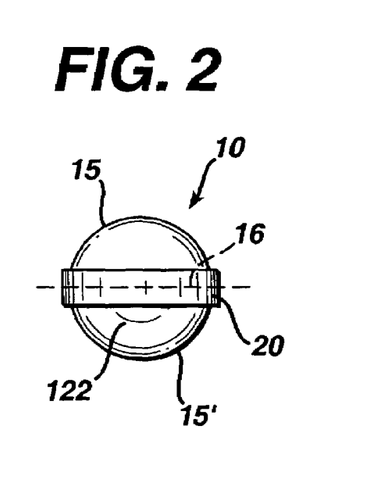
FIG. 2 is an enlarged, schematic elevational end view of the oblong convex core of FIGS. 1A and 1B, the opposite elevational end view being identical thereto.
Figure 3:
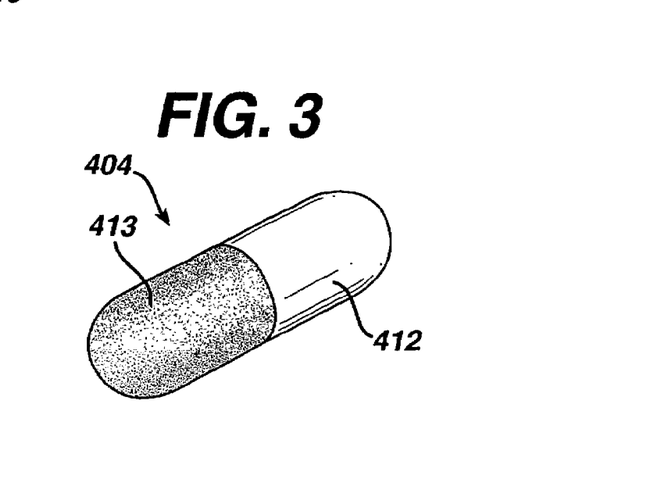
FIG. 3 is a perspective view of an exemplary tablet 404 of the present invention having a first coating portion 412 of one visual distinction and a second coating portion 413 having a second visual distinction.

In yet a further embodiment, the exterior coating layer may be comprised of a plurality of coating portions. An example of this embodiment comprised of two exterior coating portions is illustrated in FIG. 2, in which the dosage form 404 is coated with a first exterior coating portion 412 and a second exterior coating portion 413. Although the dosage form in FIG. 2 indicates that at least one of such portions is visually and/or chemically distinct from at least one other portion, it is conceived that one or more of the portions may be visually and/or chemically similar in nature. For example, each end of a tablet may be coated with dip coatings of different colors to provide a distinctive appearance for specialty products. See U.S. Pat. No. 4,820,524, which is incorporated by reference herein. In one such embodiment, the exterior coating layer comprises a first exterior coating portion and a second exterior coating portion which may be visually distinct from one another, for example the visually distinct portions may be of different colors, hues, glosses, reflective qualities, brightness, depth, shades, chroma, opacity, etc. For example, the shell may have a red portion and a yellow portion, or a flat finish portion and a glossy portion, or an opaque portion and a translucent portion.

Various types of substrates, e.g. cores, may be coated with the film forming composition of the present invention. The core or substrate may be any dosage form in need of a shiny, hard, and/or smooth surface. Examples of such coated substrates may nonexclusively result in the following products: pharmaceutical dosage forms, confectionary products, nutritional supplements, food stuffs, dyestuffs, dietary supplements, and the like.

Figure 1A:
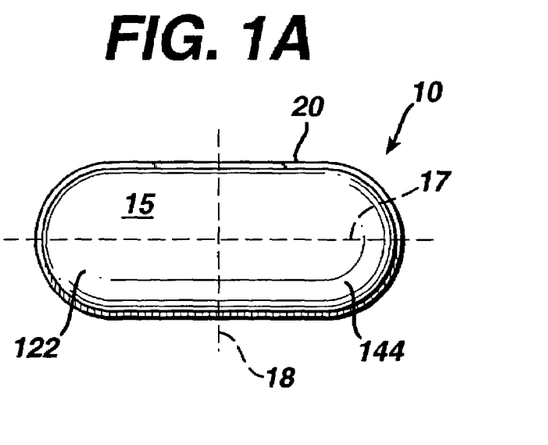
FIG. 1A is an enlarged, schematic top plan view of an oblong convex core of a first configuration, the bottom plan view being identical thereto.
Figure 1B:
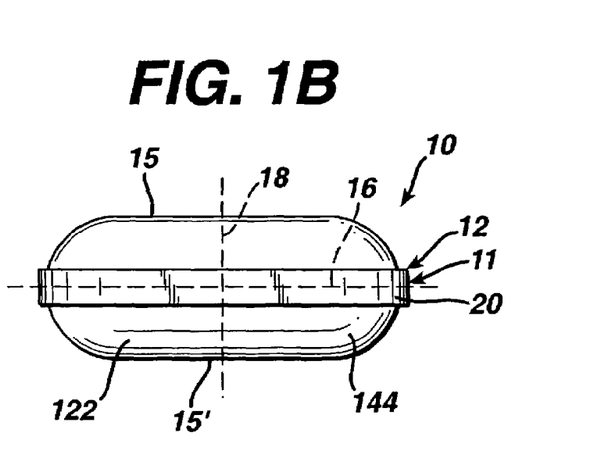
FIG. 1B is an enlarged, schematic elevational side view of the oblong convex core of FIG. 1A, having a face 15, a "belly band" or side 11, and an edge or corner 12, the opposite elevational side view being identical thereto.

The core, or substrate, of the present invention may be a solid or semi-solid dosage form of any size or shape. Suitable cores include compressed or molded tablets, hard or soft capsules, suppositories, and confectionery based forms which include, but are not limited to, lozenges, nougats, or fondants, and the like. For example, FIGS. 1A, 1B and 2 illustrate an oblong convex core 10 having an oblong shape and two rounded ends 122, 144, as viewed from the top, bottom or sides (see FIGS. 1A and 1B). The oblong convex core 10 may also have two oppositely positioned convex surfaces 15, 15' and a raised portion therebetween, referred to as a land 20 (shown most clearly in FIGS. 1B and 2).

It is noted that the length of the oblong core 10 is an imaginary line (not shown per se, but which is commensurate with a portion of the dotted line 10 that is within the core 10 shown in FIG. 1B) which extends the distance between the ends 122, 144 of the oblong core 10. The height of the oblong core 10 is another imaginary line (not shown per se, but which is commensurate with a portion of the dotted line 18 that is within the core 10 shown in FIG. 1B) which extends the distance between the two opposite convex surfaces 15, 15' of the core 10, midway of the length. The width of the oblong core is a third imaginary line (not shown per se, but which is commensurate with a portion of the dotted line 10 that is within the core 10 shown in FIG. 2) which extends the distance between opposite sides of the core 10, perpendicular to and midway of the core's length and height (and which may intersect the land 20 of the core 10, if present).

The use of subcoatings is well known in the art and disclosed in, for example, U.S. Pat. Nos. 3,185,626, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643, 894, 4,828,841, 4,725,441, 4,802,924, 5,630,871, and 6,274, 162, which are all incorporated by reference herein. Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating may be comprised of, based upon the total weight of the subcoating, from about 2 percent to about 8 percent, e.g. from about 4 percent to about 6 percent of a water-soluble cellulose ether and from about 0.1 percent to about 1 percent, castor oil, as disclosed in detail in U.S. Pat. No. 5,658,589, which is incorporated by reference herein. In another embodiment, the subcoating may be comprised of, based upon the total weight of the subcoating, from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400.

The dried subcoating typically is present in an amount, based upon the dry weight of the core, from about 0 percent to about 5 percent. The dried dip coating layer typically is present in an amount, based upon the dry weight of the core and the optional subcoating, from about 1.5 percent to about 10 percent.

The average thickness of the dried exterior coating layer typically is from about 40 to about 400 microns. However, one skilled in the art would readily appreciate without undue experimentation that the exterior coating thickness may be varied in order to provide a smoother, easier to swallow, dosage form or to achieve a desired dissolution profile. In embodiments in which the exterior coating is applied by dipping, the thickness of dipped film coatings may vary at different locations on the substrate depending upon its shape. For example, the thickness of a gelatin dipped coating at an edge or corner (see, e.g., edge 12 in FIG. 1) of a substrate may be as much as 50 percent to 70 percent less than the thickness of that coating near the center of a major face of the substrate (see, e.g. face 15 in FIG. 1). This difference can be minimized by, for example, use of a thicker subcoating, or use of dipping compositions that result in higher weight gains on the substrate. However, unlike gelatin-based coatings, the coatings comprised of the composition of the present invention have relatively less variance in thickness when applied to a substrate, and in particular when applied via dip coating to the substrate.

In embodiments wherein a thicker dip coating is desired, we have found that an effective amount of a weight gain enhancer selected from the group consisting of simethicone, polysorbate 80 and mixtures thereof, may be added to the film forming composition. The weight gain enhancer is used in an amount sufficient to increase the weight gain of the coating solution, e.g. by at least about 10 percent, by at least about 20%, or by at least about 30% on a substrate when dried. The percent weight gain increase is determined based upon the difference between the total weight of the coated substrate with the coating composition including the weight gain enhancer, and the total weight of an coated equivalent substrate, which has been coated under similar processing conditions with a coating composition that does not include an effective amount of weight gain enhancer.

A suitable film forming composition capable of achieving increased weight gain of dip coating on a substrate may contain, based upon the total dry weight of the film forming composition, from about 10 percent to about 70 percent, e.g. from about 40 percent to about 65 percent of an acrylic polymeric film former; from about 2 percent to about 20 percent, e.g. from about 5 percent to about 15 percent, of a primary plasticizer; from about 1 percent to about 50 percent, e.g. from about 15 percent to about 35 percent of a secondary plasticizer; and from about 0.01 percent to about 0.25 percent, e.g. from about 0.03 percent to about 0.15 percent of a weight gain enhancer. When aesthetics of the final tablet are of particular concern, it is recommended to not use greater than about 0.25 percent of a weight gain enhancer.

The film forming compositions of the present invention may be prepared by mixing all film formers under ambient conditions until the resulting mixture is homogeneous. The primary plasticizers are then added thereto at a temperature of about 55° C. to about 70° C. to form a first mixture. In an independent container, the secondary plasticizer is combined with the solvent in an amount sufficient to dissolve the secondary plasticizer and under ambient conditions. This mixture is then added to the first mixture at a temperature of about 55° C. to about 70° C. Any remaining solvent and any optional ingredients such as colorants, opacifiers, the weight gain enhancer, or other ingredients are then added thereto and mixed in the mixer until homogeneous under ambient conditions.

The film forming composition of the present invention may be applied to the substrate by any suitable method capable of producing a smooth film surface thereon. Examples of suitable methods include, but are not limited to molding or dipping. One suitable molding method includes forming a sheet of the film-forming composition, then enrobing the tablet therewith as described in, for example, U.S. Pat. Nos. 5,146,730 and 5,459,983, which are incorporated by reference. Another suitable molding method includes introducing the film forming composition in a flowable form around a substrate in a mold cavity, then hardening the film-forming composition (e.g. by cooling), so as to form a coating on the substrate. After the dosage form is removed from the mold, it optionally may be dried. In one particular embodiment, the film forming composition of the invention may be injected through an orifice into a mold cavity, which contains the substrate.

It has surprisingly been found that substrates may be dipped into such dispersions of the present invention using the same equipment and similar range of process conditions as used for the production of dip molded, gelatin-coated tablets. For example, both tablets and hard capsules may be coated using the aqueous dispersions of the present invention via known gelatin-dipping process parameters and equipment. Details of such equipment and processing conditions are known in the art and are disclosed at, for example, U.S. Pat. No. 4,820,524, which is incorporated by reference herein. Advantageously, because the coating solutions of the present invention are fluid at room temperature and are less susceptible to microbial growth than gelatin compositions, the dip coating process may occur under ambient temperature and pressure conditions.

The dosage forms coated with the composition of the present invention may contain one or more active agents. The term "active agent" is used herein in a broad sense and may encompass any material that can be carried by or entrained in the system. For example, the active agent can be a pharmaceutical, nutraceutical, vitamin, dietary supplement, nutrient, herb, foodstuff, dyestuff, nutritional, mineral, supplement, or favoring agent or the like and combinations thereof.

The active agents useful herein can be selected from classes from those in the following therapeutic categories: ace-inhibitors; alkaloids; antacids; analgesics; anabolic agents; anti-anginal drugs; anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics; anti-migraine agents; antinauseants; antipsychotics; antistroke agents; antithyroid preparations; anabolic drugs; antiobesity agents; antiparasitics; antipsychotics; antipyretics; antispasmodics; antithrombotics; antitumor agents; antitussives; antiulcer agents; anti-uricemic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

Active agents that may be used in the invention include, but are not limited to: acetaminophen; acetic acid; acetylsalicylic acid, including its buffered forms; acrivastine; albuterol and its sulfate; alcohol; alkaline phosphatase; allantoin; aloe; aluminum acetate, carbonate, chlorohydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; bromopheniramine and its maleate; buspirone; caffeine; calamine; calcium carbonate, casinate and hydroxide; camphor; captopril; cascara sagrada; castor oil; cefaclor; cefadroxil; cephalexin; centrizine and its hydrochloride; cetirizine; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine; cinnamedrine hydrochloride; citalopram; citric acid; clarithromycin; clemastine and its fumarate; clonidine; clorfibrate; cocoa butter; cod liver oil; codeine and its fumarate and phosphate; cortisone acetate; ciprofloxacin HCl; cyanocobalamin; cyclizine hydrochloride; cyproheptadine; danthron; dexbromopheniramine maleate; dextromethorphan and its hydrohalides; diazepam; dibucaine; dichloralphenazone; diclofen and its alkali metal sales; diclofenac sodium; digoxin; dihydroergotamine and its hydrogenates/mesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fexofenadine; fluoxetine; folic acid; fosphenytoin; 5-fluorouracil (5-FU); fluoxetine; flurbiprofen; furosemide; gabapentan; gentamicin; gemfibrozil; glipizide; glycerine; glyceryl stearate; granisetron; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its mono- and dinitrates; isoxicam; ketamine; kaolin; ketoprofen; lactic acid; lanolin; lecithin; leuprolide acetate; lidocaine and its hydrochloride salt; lifinopril; liotrix; loperamide, loratadine; lovastatin; luteinizing hormore; LHRH (lutenizing hormone replacement hormone); magnesium carbonate, hydroxide, salicylate, and trisilicate; meclizine; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methsergide and its maleate; methyl nicotinate; methyl salicylate; methyl cellulose; methsuximide; metoclopramide and its halides/hydrates; metronidazole; metoprotol tartrate; miconazole nitrate; mineral oil; minoxidil; morphine; naproxen and its alkali metal sodium salts; nifedipine; neomycin sulfate; niacin; niacinamide; nicotine; nicotinamide; nimesulide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine; phenytoin; pirmenol; piroxicam and its salts; polymicin B sulfate; potassium chloride and nitrate; prazepam; procainamide hydrochloride; procaterol; promethazine and its hydrochloride; propoxyphene and its hydrochloride and napsylate; pramiracetin; pramoxine and its hydrochloride salt; prochlorperazine and its maleate; propanolol and its hydrochloride; promethazine and its hydrochloride; propanolol; pseudoephedrine and its sulfates and hydrochlorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline; terfenadine; thiethylperazine and its maleate; timolol and its maleate; thioperidone; tramadol; trimetrexate; triazolam; tretinoin; tetracycline hydrochloride; tolmetin; tolnaftate; triclosan; trimethobenzamide and its hydrochloride; tripelennamine and its hydrochloride; tripolidine hydrochloride; undecylenic acid; vancomycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Active agents may further include, but are not limited to food acids; insoluble metal and mineral hydroxides, carbonates, oxides, polycarbophils, and salts thereof; adsorbates of active drugs on a magnesium trisilicate base and on a magnesium aluminum silicate base, and mixtures thereof. Mixtures and pharmaceutically acceptable salts of these and other actives can be used.

In one embodiment, the dosage forms coated with the dip coatings of the present invention may be provided for immediate release of the active ingredient, i.e. the dissolution of the dosage form conformed to USP specifications for immediate release tablets containing the particular active ingredient employed. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999).

We have unexpectedly found that the coatings, which were formed by applying the compositions of the present invention onto substrates, possessed excellent properties comparable to those possessed by gelatin coatings, e.g. crack resistance, hardness, thickness, color uniformity, smoothness, and gloss. In one embodiment, the exterior layer or "shell" of the present invention advantageously possesses a high surface gloss. The surface gloss of the shell and/or the exterior surface of the dosage form is at least about 150 gloss units, e.g. at least about 175 gloss units, or at least about 190 gloss units when measured by the method set forth in Example 4 herein.

In addition, substrates dip coated with the compositions of the present invention were superior to substrates dip coated with conventional gelatin-based coatings in several important ways. First, substrates dip coated with the compositions of the present invention advantageously retained acceptable dissolution characteristics for the desired shelf-life and storage period at elevated temperature and humidity conditions. In particular, the compositions according to the present invention were also advantageously more resistant to microbial growth, which thereby enabled a longer shelf-life or use-life of the dipping solution as well as a reduction in manufacturing cost. Second, the dried coatings comprised of the compositions of the present invention also surprisingly and advantageously contained fewer air bubbles relative to the amount present in dried, gelatin based dipping compositions, and possessed a relatively more uniform coating thickness, i.e., the thickness at the tablet edges 11 is comparable to that at the face 15 as shown in the tablet 10 illustrated in FIG. 2. Third, unlike dip processing with gelatin-containing compositions, substrates may optionally be dipped in the solutions of the present invention at room temperature, which is economically more beneficial. Fourth, the dip coated compositions of the present invention possessed a higher degree of glossiness relative to similar coatings applied via spray coating methods known in the art. The dip coated compositions of the present invention also possessed a similar degree of glossiness relative to that possessed by gelatin-containing dip or enrobing coatings, which are currently viewed as the industry benchmark for high gloss coatings. See, e.g., U.S. Pat. No. 6,274,162 (Typical gloss readings for standard, commercially available gel-dipped or gelatin enrobed tablets range from about 200 to 240 gloss units, gloss readings for standard, commercially available sugar-coated medicaments range from 177 to 209 gloss units, and gloss readings for a new, high-gloss coating system range from about 148 to about 243 gloss units.).

We have further unexpectedly found that the addition of an effective amount of weight gain enhancer to the film forming composition of the present invention not only significantly increased the resulting dry weight of the dip coating on a substrate, but it also improved the color uniformity of the coating.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Example 1

Preparation of Dip Coating Dispersions

An aqueous dispersion containing the ingredients set forth in Table A was prepared:

TABLE A

Aqueous Dispersion Dipcoating Composition

| Ingredient | Amount (g) |
| --- | --- |
| poly(ethyl acrylate, methyl methacrylate) trimethylammonioethyl methacrylate chloride from Rohm Pharma under the tradename, "Eudragit RL30D" *(30% dispersion) | 100.0* |
| Methyl paraben | 5.0 |
| Polyvinylpyrollidone from BASF Aktiengesellschaft under the tradename, "K-90" | 12.0 |
| water | 60.0 |
| Red #55 dye | 1.0 |
| Red #40 lake | 0.5 |
| PEG 400 | 4.0 |
| Total Solution Weight | 182.5 |
| solids in coating solution | 52.5 g (28.78%) |

A second aqueous dispersion containing the ingredients set forth in Table B was prepared:

TABLE B

Aqueous Dispersion Dipcoating Composition

| Ingredient | Amount (g) |
| --- | --- |
| poly(ethyl acrylate, methyl methacrylate) trimethylammonioethyl methacrylate chloride from Rohm Pharma under the tradename, "Eudragit RL30D" (*30% dispersion) | 100.0* |
| Methyl paraben | 5.0 |
| Polyvinylpyrollidone from BASF Aktiengesellschaft under the tradename, "K-90" | 12.0 |
| water | 110 |
| "Opatint" ® yellow color obtained from Colorcon, Inc. | 3.0 |
| PEG 400 | 4.0 |
| Total Solution Weight | 234 |
| solids in coating solution | 54 g (23.07%) |

The red colorant-containing dispersion was independently prepared by placing the Eudragit RL30D in a 400 ml beaker, then adding 60 g of water followed by the 4 g of PEG 400 thereto under ambient conditions with mixing using a electric mixer (Janke and Kunkel, IKA Labortechnik, Staufen, Germany) with propeller blade at approximately 700 rpm. After adding the methylparaben thereto, the resulting solution was heated to 60° C. with constant mixing. While the resulting solution was cooling, the polyvinylpyrollidone was added thereto with mixing until dissolved. When the viscosity of the solution increased to the point that the vortex was no longer visually apparent, the speed of the mixer was increased to 1200 rpm. The colorants were added thereto with mixing until homogeneous. Each resulting solution was deaerated overnight under ambient conditions.

The yellow-colorant dispersion was made in an independent beaker in accordance with the same procedure, except with substitution of 110 g of water in place of the 60 g of water.

Example 2

Preparation of Subcoating Dispersion

An aqueous dispersion containing the ingredients set forth in Table C was prepared by combining all of the ingredients in a beaker under ambient conditions.

TABLE C

| Aqueous Dispersion Subcoating Composition | |
|---|---|
| Ingredient | Part* |
| HPMC (2910, 5 mPs) from Dow Chemical Company under the tradename, "Methocel E-5" | 20 |
| Castor oil | 1 |
| Water | 241.5 |
| Total Coating Solution | 262.5 |
| % solids in coating solution | 8% |

*expressed in terms of part by weight unless otherwise noted

Example 3

Preparation of Dipcoated Tablets

Compressed tablets were prepared in accordance with the procedure set forth in Example 1 of U.S. Pat. No. 5,658,589 ("'589 Patent"), which was incorporated by reference herein.

The subcoating dispersion of Example 2 was then applied onto the compressed tablets via spraying in accordance with the procedure set forth in the examples of the '589 Patent. The dried subcoated tablets weighed an average of about 4.5% more than the subcoating-free tablets, i.e. the amount of subcoating was about 4.5% of the weight of the uncoated cores.

One half of each of these subcoated tablets were hand-dipped into the first dip coating dispersion of Example 1 for a dwell time of 1 second, removed from the dipping solution, then dried under ambient conditions. For each tablet, this process was repeated; the other half of each coated tablet was coated with the second dip coating dispersion of Example 1. The weight gain for these tablets is shown in Table D below:

TABLE D

| | % Weight Gain of Dried Subcoated Tablets | | |
|---|---|---|---|
| Tablet Number | Weight increase (Yellow dip) (g) | Weight increase (Red dip) (g) | Weight increase (Yellow and Red dip combined) (g) |
| 1 | 0.111 | 0.017 | 0.026 |
| 2 | 0.014 | — | — |
| 3 | 0.012 | 0.019 | 0.031 |
| 4 | 0.011 | 0.019 | 0.030 |
| 5 | 0.011 | — | — |
| 6 | 0.010 | 0.019 | 0.029 |
| 7 | — | 0.017 | — |
| Average Weight Gained | 0.011 | 0.018 | 0.030 |

This example showed that the tablets prepared in accordance with this example possessed an elegant, uniform color as well as good, uniform edge coverage. These tablets also were non-tacky and resembled gelatin-dip coated tablets.

Example 4

Surface Gloss Measurement of Coated Tablets

Tablets made according to the preceding examples were tested for surface gloss using an instrument available from TriCor Systems Inc. (Elgin, Ill.) under the tradename, "Tri-Cor Model 805A/806H Surface Analysis System" and generally in accordance with the procedure described in "TriCor Systems WGLOSS 3.4 Model 805A/806H Surface Analysis System Reference Manual" (1996), which is incorporated by reference herein, except as modified below, This instrument utilized a CCD camera detector, employed a flat diffuse light source, compared tablet samples to a reference standard, and determined average gloss values at a 60 degree incident angle. During its operation, the instrument generated a grey-scale image, wherein the occurrence of brighter pixels indicated the presence of more gloss at that given location.

The instrument also incorporated software that utilized a grouping method to quantify gloss, i.e., pixels with similar brightness were grouped together for averaging purposes.

The "percent full scale" or "percent ideal" setting (also referred to as the "percent sample group" setting), was specified by the user to designate the portion of the brightest pixels above the threshold that will be considered as one group and averaged within that group. "Threshold", as used herein, is defined as the maximum gloss value that will not be included in the average gloss value calculation. Thus, the background, or the non-glossy areas of a sample were excluded from the average gloss value calculations. The method disclosed in K. Fegley and C. Vesey, "The Effect of Tablet Shape on the Perception of High Gloss Film Coating Systems", which is available at www.colorcon.com as of 18 Mar. 2002 and incorporated by reference herein, was used in order to minimize the effects resulting from different tablet shapes, and thus report a metric that was comparable across the industry.(Selected the 50% sample group setting as the setting which best approximated analogous data from tablet surface roughness measurements.).

After initially calibrating the instrument using a calibration reference plate (190-228; 294 degree standard; no mask, rotation 0, depth 0), a standard surface gloss measurement was then created using gel-coated caplets available from McNEIL-PPC, Inc. under the tradename, "Extra Strength Tylenol Gelcaps." The average gloss value for a sample of 112 of such gel-coated caplets was then determined, while employing the 25 mm full view mask (190-280), and configuring the instrument to the following settings:

Rotation: 0
Depth: 0.25 inches
Gloss Threshold: 95
% Full Scale: 50
Index of Refraction: 1.57

The average surface gloss value for the reference standard was determined to be 269 gloss units.

Samples of coated tablets prepared according to the Example 2 were then tested in accordance with the same procedure. The surface gloss values that were obtained are summarized in Table E below.

TABLE E

Gloss values of coated tablets

| Example No. | 2 |
|---|---|
| Type of coating | dipped |
| No. of tablets tested | 2 |
| Gloss Value (g.u.) | 244 |

Additional samples of other, commercially available gel coated tablets were also tested in accordance with the same procedure and compared to the same standard. The results are summarized in Table F below.

TABLE F

Gloss values of commercially available coated tablets

| Product | Motrin IB * Caplet (white) | Excedrin* * Aspirin free Caplets (red) | Excedrin ** Migraine Geltab (green side) | Excedrin ** Migraine Geltab (white side) | Extra Strength Tylenol Geltabs * (yellow side) | Extra Strength Tylenol Geltabs * (red side) |
|---|---|---|---|---|---|---|
| Type of coating | sprayed film | sprayed film | gelatin enrobed | gelatin enrobed | dipped | dipped |
| No. of tablets tested | 41 | 40 | 10 | 10 | 112 | 112 |
| Gloss Value (g.u.) | 125 | 119 | 270 | 264 | 268 | 268 |

* Available from McNEIL-PPC, Inc.
** Available from Bristol-Myers, Squibb, Inc.

This Example showed that the tablets coated with the compositions of the present invention possessed a high surface gloss value that either was comparable to or exceeded that possessed by commercially—available gelatin coated tablets. In contrast, typical sprayed films possessed a substantially lower surface gloss, e.g. 119 to 125 in this Example.

Example 5

Preparation of Dip Coating Dispersion with Simethicone

The dispersion having the formulation set forth below in Table G is prepared in accordance with the procedure set forth in Example 1, but with the simethicone being added to the mixture after the polyvinylpyrollidone is dissolved therein.

TABLE G

Aqueous Dispersion Subcoating Composition with Simethicone

| Ingredient | Amount (g) |
|---|---|
| poly(ethyl acrylate, methyl methacrylate)trimethylammonioethyl methacrylate chloride from Rohm Pharma under the tradename, "Eudragit RL30D" | 100.0 |
| Methyl paraben | 5.0 |
| Polyvinylpyrollidone from BASF Aktiengesellschaft under the tradename, "K-90" | 12.0 |
| Simethicone | 0.18 g (0.15% of dry weight) |
| water | 60.0 |

TABLE G-continued

Aqueous Dispersion Subcoating Composition with Simethicone

| Ingredient | Amount (g) |
|---|---|
| Red #55 dye | 1.0 |
| Red #40 lake | 0.5 |
| PEG 400 | 4.0 |
| Total Solution Weight | 182.8 |
| % solids in coating solution | 52.68 g (28.8%) |

This Example is repeated with various amounts of simethicone ranging from, based upon the total dry weight of the film forming composition, about 0.03 to about 0.15 percent.

Example 6

Preparation of Dip Coated Tablets

Tablets are subcoated with the subcoating of Example 2, then are dip coated with the dispersion of Example 5 using the procedure set forth in Example 3.

I claim:

1. A pharmaceutical dosage form comprised of:
   a) a core having a surface; and
   b) a film forming composition covering at least a portion of the surface, said film forming composition comprised of, based upon the total dry solids weight of the composition:
      a) from about 10 percent to about 70 percent of a film former comprised of a polymer or copolymer comprised of repeat units selected from the group consisting of acrylic acid, ethyl acrylate, methyl methacrylate, trimethylammonioethyl methacrylate chloride, and methacylic acid, or a mixture of such polymer or copolymer;
      b) from about 2 percent to about 20 percent of a primary plasticizer which is a paraben; and
      c) from about 1 percent to about 50 percent of a secondary plasticizer selected from the group consisting of polyvinylpyrrolidone, polyethylene glycol 300, polyethylene glycol 400, pharmaceutically acceptable salts thereof, and mixtures thereof;
   wherein the composition possesses a surface gloss of at least 150 when applied via dip coating to the surface of the core.

2. The pharmaceutical dosage form of claim 1, wherein the film former is selected from the group consisting of
a polymer or copolymer comprised of repeat units selected from the group consisting of methacrylic acid, methyl methacrylate, or trimethylammonioethyl methacrylate chloride; and
mixtures thereof.

3. The pharmaceutical dosage form of claim 1, wherein the film former is ammoniomethacrylata copolymer.

4. The pharmaceutical dosage form of claim 1, wherein the film former is selected from the group consisting of:
a) poly(ethyl acrylate, methyl methacrylate, trimethylammonioethyl methacrylate chloride) in a 1:2:0.1 weight ratio;
b) poly(methacrylic acid, methyl methacrylate) in a 1:2 weight ratio;
c) poly(methacrylic acid, methyl methacrylate) in a 1:1 weight; and
d) mixtures thereof.

5. The pharmaceutical dosage form of claim 1, wherein the film former is selected from the group consisting of:
a) poly(ethyl acrylate, methyl methacrylate, trimethylammonioethyl methacrylate chloride);
b) poly(methacrylic acid, ethyl acrylate);
c) poly(ethyl acrylate, methyl methacrylate);
d) poly(methacrylic acid, methyl methacrylate), and
e) mixtures thereof.

6. The pharmaceutical dosage form of claim 1 wherein the paraben is selected from the group consisting of methyl paraben, ethyl paraben, propyl paraben, butyl paraben, pharmaceutically available salts thereof, and mixtures thereof.

7. The pharmaceutical dosage form of claim 1 wherein the secondary plasticizer is polyvinylpyrrolidone.

8. The pharmaceutical dosage form of claim 1, wherein the composition is substantially free of gelatin.

9. The pharmaceutical dosage form of claim 1, wherein the composition is further comprised of, based upon the total dry weight of the composition, from about 0 percent to about 14 percent of a coloring agent.

10. The pharmaceutical dosage form of claim 9 wherein the coloring agent is selected from the group consisting of azo dyes, quinopthalone dyes, triphenylmethane dyes, xanthene dyes, indigoid dyes, iron oxides, iron hydroxides, titanium dioxide, natural dyes, and mixtures thereof.

11. The pharmaceutical dosage form of claim 1 further comprising a plurality of exterior coatings, wherein at least a first portion of the dosage form is comprised of a first exterior coating and at least a second portion of the dosage form is comprised of a second exterior coating.

12. The pharmaceutical dosage form of claim 11 wherein the second exterior coating is visually distinct from the first exterior coating.

13. A pharmaceutical dosage form comprising a core, a subcoating substantially covering said core, and an exterior coating substantially covering said subcoating, wherein the exterior coating is comprised of a film forming composition comprised of, based upon the total dry solids weight of the composition:
a) from about 10 percent to about 70 percent of a film former comprised of a polymer or copolymer comprised of repeat units selected from the group consisting of acrylic acid, ethyl acrylate, methyl methacrylate, trimethylammonioethyl methacrylate chloride, and methacrylic acid, or a mixture of such polymer or copolymer;
b) from about 2 percent to about 20 percent of a primary plasticizer which is a paraben; and
c) from about 1 percent to about 50 percent of a secondary plasticizer selected from the group consisting of polyvinylpyrrolidone, polyethylene glycol 300, polyethylene glycol 400, pharmaceutically acceptable salts thereof, and mixtures thereof.

14. The coated dosage form of claim 13 wherein the subcoating is selected from the group consisting of cellulose ethers, plasticizers, polycarbohydrates, pigments, opacifiers, and mixtures thereof.

15. The pharmaceutical dosage form of claim 1 in the form of a tablet or caplet.

16. The pharmaceutical dosage form of claim 1 comprising an effective amount of a pharmaceutical active ingredient, wherein said dosage form meets USP dissolution requirements for immediate release forms of said pharmaceutical active ingredient.

17. A method of making coated pharmaceutical tablets comprising dip coating pharmaceutical tablets with an aqueous dispersion under conditions sufficient to form a coating on the tablets, said aqueous dispersion comprised of, based upon the total weight of the dispersion,
a) from about 10 percent to about 70 percent of a film former comprised of a polymer or copolymer comprise of repeat units selected from the group consisting of acrylic acid, ethyl acrylate, methyl methacrylate, trimethylammonioethyl methacrylate chloride, and methacrylic acid, or a mixture of such polymer or copolymer;
b) from about 2 percent to about 40 percent of a primary plasticizer which is a paraben;
c) from about 5 percent to about 20 percent of a secondary plasticizer selected from the group consisting of polyvinylpyrrolidone, polyethylene glycol 300, polyethylene glycol 400, pharmaceutically acceptable salts thereof, and mixtures thereof; and
d) from about 5 percent to about 30 percent of water,
wherein the coating possesses a surface gloss of at least 150 when applied via dip coating to the tablet.

18. A pharmaceutical dosage form comprising a core and a coating, said coating covering at least a portion of said core and having a surface gloss of at least 150 gloss units, wherein the coating comprises
a) from about 40 percent to about 65 percent of a film former comprised of a polymer or copolymer comprised of repeat units selected from the group consisting of acrylic acid, ethyl acrylate, methyl methacrylate, trimethylammonioethyl methacrylate chloride, and methacrylic acid, or a mixture of such polymer or copolymer;
b) from about 5 percent to about 15 percent of a primary plasticizer which is a paraben; and
c) from about 15 percent to about 35 percent of a secondary plasticizer selected from the group consisting of polyvinylpyrrolidone, polyethylene glycol 300, polyethylene glycol 400, pharmaceutically acceptable salts thereof, and mixtures thereof.

19. A simulated capsule-like medicament comprising:
a.) a core having a first end and a second end,
b.) a first coating layer having a first visual distinction provided on said first end of said tablet core; and
c.) a second coating layer having a second visual distinction on said second end of said tablet core;
wherein at least one of said first coating layer and second coating layer is comprised of, based upon the total dry solids weight of the composition:
(i) from about 10 percent to about 70 percent of a film former comprised of a polymer or copolymer comprises repeat units selected from the group consisting of acrylic acid, ethyl acrylate, methyl methacrylate, trimethylammonioethyl methacrylate chloride, and methacylic acid, or a mixture of such polymer or copolymer;
(ii) from about 2 percent to about 20 percent of a primary plasticizer which paraben; and
(iii) from about 1 percent to about 50 percent of a secondary plasticizer selected from the group consisting of polyvinylpyrrolidone, polyethylene glycol 300, polyethylene glycol 400, pharmaceutically acceptable salts thereof, and mixtures thereof.

20. The medicament of claim 19 wherein the second visual distinction is visually different from said first visual distinction.

21. The medicament of claim 20 wherein the first visual distinction is a first color, and the second visual distinction is a second color.

22. The medicament of claim 19 further comprising a subcoating layer substantially covering said core, said subcoating layer provided between said core and said first coating layer and said second coating layer.

23. The medicament of claim 22 wherein the subcoating is selected from the group consisting of cellulose ethers, plasticizers, polycarbohydrates, pigments, opacifiers, and mixtures thereof.

24. The pharmaceutical dosage form of claim 1 wherein the film former is a mixture comprising a polymer or copolymer of acrylic acid or derivative thereof.

25. The pharmaceutical dosage form of claim 1 wherein the film former is a copolymer comprising a polymer or copolymer of acrylic acid or derivative thereof.

* * * * *